(12) United States Patent
De Clerck

(10) Patent No.: US 8,632,337 B2
(45) Date of Patent: Jan. 21, 2014

(54) METHOD AND MARKER ELEMENT TO DETERMINE THE POSITION OF A DENTAL IMPLANT

(75) Inventor: Rene De Clerck, Tervuren (BE)

(73) Assignee: Dental Vision BVBA, Tervuren (BE)

( * ) Notice: Subject to any disclaimer, the term of this patent is extended or adjusted under 35 U.S.C. 154(b) by 428 days.

(21) Appl. No.: 10/590,824

(22) PCT Filed: Feb. 25, 2005

(86) PCT No.: PCT/IB2005/050694
§ 371 (c)(1), (2), (4) Date: Aug. 25, 2006

(87) PCT Pub. No.: WO2005/084576
PCT Pub. Date: Sep. 15, 2005

(65) Prior Publication Data
US 2007/0141531 A1   Jun. 21, 2007

(30) Foreign Application Priority Data
Feb. 25, 2004   (BE) .................................. 2004/0104

(51) Int. Cl.
*A61C 5/00*   (2006.01)
*A61C 3/00*   (2006.01)

(52) U.S. Cl.
USPC ........................................... 433/215; 433/75

(58) Field of Classification Search
USPC ............. 433/173–174, 72, 75, 215; 606/102, 606/329, 331, 912, 916; 378/15, 162; 382/131; 623/1.34; 600/426
See application file for complete search history.

(56) References Cited

U.S. PATENT DOCUMENTS

| 4,349,498 | A | * | 9/1982 | Ellis et al. ...................... 264/81 |
| 5,208,845 | A | | 5/1993 | Gelb |
| 5,668,844 | A | * | 9/1997 | Webber ............................ 378/2 |
| 5,989,258 | A | | 11/1999 | Hatrori |
| 6,073,044 | A | * | 6/2000 | Fitzpatrick et al. ........... 600/426 |
| 6,333,971 | B2 | * | 12/2001 | McCrory et al. .............. 378/162 |
| 2003/0170588 | A1 | * | 9/2003 | Augthun et al. ................ 433/72 |
| 2005/0043735 | A1 | * | 2/2005 | Ahmad ............................ 606/73 |
| 2005/0059972 | A1 | * | 3/2005 | Biscup ............................ 606/73 |

FOREIGN PATENT DOCUMENTS

EP           0 231 838 A2    8/1987

* cited by examiner

*Primary Examiner* — Heidi M Eide
(74) *Attorney, Agent, or Firm* — Browdy and Neimark, PLLC

(57) ABSTRACT

A method and marker element to determine the position of a prosthetic element (2) which is fixed to the jaw (13) of a person, such as a dental implant. An image is formed of the jaw of a reproduction model of this jaw which is provided with the prosthetic element (2), by means of X-rays or magnetic resonance. At least one marker element (3) is then provided on the prosthetic element (2) which produces a strong contrast in imaging techniques. The position of the marker is then formed by X-rays or by magnetic resonance, and the position of the prosthetic element (2) is then derived from the observed position of the marker element (3).

16 Claims, 1 Drawing Sheet

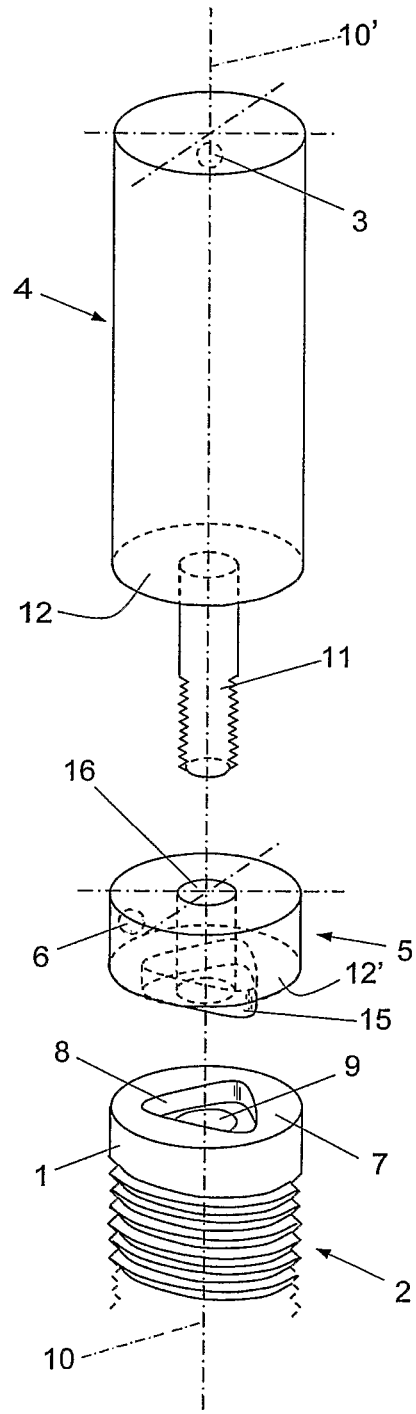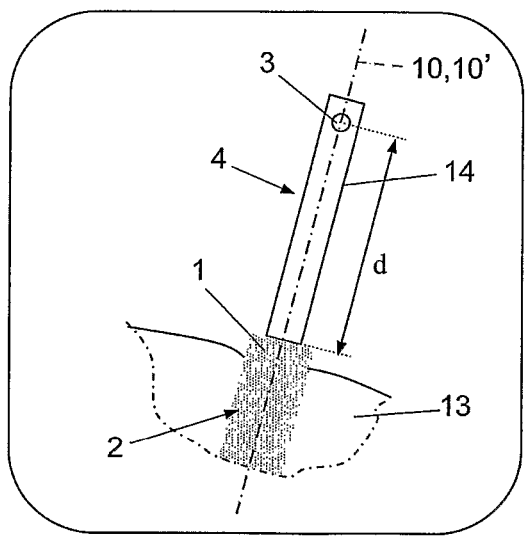
Fig. 1
Fig. 2

METHOD AND MARKER ELEMENT TO DETERMINE THE POSITION OF A DENTAL IMPLANT

BACKGROUND OF THE INVENTION

1. Technical Field of the Invention

The invention concerns a method to determine the position of a dental implant, which is fixed to the bone of the jaw of a person, in relation to said jaw, whereby an image is formed of the jaw or of a reproduction model of this jaw with the prosthetic element by means of X-rays or magnetic resonance (NMR).

2. Prior Art

More particularly, when manufacturing dental prostheses which are mounted on an implant in the oral cavity of a patient, the implant must be precisely positioned in relation to the jaw. This is particularly the case when one wishes to manufacture a superstructure for a dental prosthesis by milling it for example out of a chunk of metal.

However, the known techniques do not allow to determine the three-dimensional position of an implant in the jaw of a person in a simple and precise manner. It is not possible, for example, to form a sharp image with sufficient contrast of an implant in a jaw by means of X-rays. From such an image obtained with X-rays, the orientation and the position of an implant cannot be derived with great precision.

OBJECT AND SUMMARY OF THE INVENTION

The invention aims to provide a method which makes it possible to determine the orientation and the position of a prosthetic element, such as a dental implant, in relation to a jaw in which this element is fixed, with very great precision.

To this aim, a marker element is fixed to said prosthetic element. This marker element produces a strong contrast when making X rays. The position of the marker element in relation to the jaw is hereby determined on the basis of the image which is formed with said X-rays. Next, the position of the above-mentioned prosthetic element is derived from the observed position of said marker element.

Practically, a support made of a material which is transparent to X-rays, in which said marker element is provided, is fixed to said prosthetic element in a detachable manner.

According to a preferred embodiment of the method according to the invention, when the prosthetic element consists of a dental implant or comprises such an implant, said support, which is preferably bar-shaped en detachable, is fixed to the free end of said implant, such that this support extends coaxially to the implant.

In an advantageous manner, use is made of a spherical marker element which is preferably made of tantalum, platinum or tungsten.

According to an interesting embodiment of the method according to the invention, said image is formed by means of computer tomography.

The invention also concerns a marker element to determine the position of a prosthetic element which is fixed to the jaw of a person, such as a dental implant, in relation to this jaw, whereby an image is formed of the jaw or of a reproduction model of this jaw with the prosthetic element by means of X-rays or another imaging technique. This marker element is characterised in that it produces a strong contrast in X rays, compared to said prosthetic element itself.

This marker element preferably mainly consists of tantalum, platinum or tungsten.

According to a specific embodiment of the marker element according to the invention, it is provided on a support having means to be fixed to said prosthetic element in a detachable manner, in a fixed position.

BRIEF DESCRIPTION OF THE DRAWINGS

Other particularities and advantages of the method and the marker element according to the invention will become clear from the following description of a few special embodiments of the invention; this description is given as an example only and does not restrict the scope of the claimed protection in any way; the reference figures used hereafter refer to the accompanying drawings.

FIG. 1 schematically represents a view in perspective with dismounted parts of an implant with marker elements and a support according to the invention.

FIG. 2 is a schematic representation of the image, formed by means of X-rays, of an implant with a marker element and a support of this element.

In the different drawings, the same reference figures refer to the same elements.

DETAILED DESCRIPTION OF THE PREFERRED EMBODIMENT OF THE INVENTION

The invention generally concerns a method to determine the position of implants which are provided in the jawbone of a patient. This position-finding makes it possible to manufacture a dental prosthesis which must be fixed to said implants. Such a dental prosthesis may comprise what is called a superstructure upon which are provided, in a manner known as such, one or several artificial teeth.

An implant is normally cylindrical and is put in the bone of a jaw, whereby a free end of this implant extends to the gingiva. On this free end, which forms the head of the implant, must thus be fixed a dental prosthesis.

Usually, after the implant has been provided, a dental prosthesis is not immediately fixed on the head thereof in order to allow the bone to grow around the implant, such that it is anchored in the jaw in a sufficiently firm and immovable manner. At the same time, the gingiva around the head of the implant can recover from the operation.

According to the known techniques, a mould is made from the jaw with the implant in order to be able to make a reproduction model thereof. This reproduction model also comprises a copy of the implant, whereby the position of this copy in relation to the model is identical to the position of the implant in relation to the jaw.

On the basis of this reproduction model is made a superstructure with accompanying artificial teeth.

According to recent developments in prosthodontics, we try to make such a dental prosthesis via what is called 'rapid prototyping' techniques, whereby for example the superstructure is made directly out of a chunk of metal by means of a fully automatic milling machine. To this end, a digital three-dimensional model of the jaw must be made beforehand, with the exact position of the implant.

Such a three-dimensional digital model is obtained for example by making a CT-scan (computer tomography scan) of the jaw or of the above-mentioned reproduction model. Of course, other imaging techniques are possible as well. The used imaging techniques make use of X-rays such that implants, which are usually made of titanium, are not clearly discernable and produce an image contrast which is insufficient to be able to precisely determine the position.

In the method according to the invention, a marker element is fixed to the implant. This marker element is characterised in that it produces a good contrast and is very sharply and clearly discernable in the formed image in case of X rays.

Thus, this marker element is formed of a material having a high absorption for X-rays, such as for example tantalum. Naturally, other materials are suitable as well to be used as marker element. It is assumed, among others, that materials having a high atomic mass and a large density produce good results, such as for example tungsten, platinum, gold, etc. The marker element preferably has a density which is larger than 10 g/cm$^3$ at 25° C. and an atomic mass which is at least equal to 100. According to a specific embodiment of the invention, the atomic mass of the marker element is more than 150 and its density is larger than 15 g/cm$^3$.

More particularly, according to the method of the invention, the marker element is fixed to the implant in a certain position and at a certain distance in relation to the latter. The position of the marker element in relation to the implant is hereby determined univocally.

To this end, this marker element is provided for example in a support in the form of a preferably cylindrical bar which is threaded on one far end, with which it is fixed to the head of the implant in a detachable manner. Thus, the bar extends, after being mounted on the implant, coaxially to the latter.

The other far end of the bar comprises said marker element. The latter is preferably spherical with for example a diameter between 1 and 3 mm, whereby its middle point is situated practically on the longitudinal axis of the cylindrical bar. The distance between the marker element and the far end of the bar, which is to be fixed to the implant, is hereby known exactly.

In an advantageous manner, the distance between this marker element and the far end of the support is measured, which far end is to be connected to the implant when it is fixed thereto.

Said support is preferably made of a material which is to a large extent transparent to X-rays.

In order to thus determine the position of the implant in relation to the jaw in which it is placed, said support is fixed with the marker element to the free end of the implant which extends in relation to the bone of the jaw. Next, an X ray is taken, in particular a three-dimensional image, of the jaw with the implant and the marker element, for example by making a CT-scan as mentioned above.

The thus obtained three-dimensional image produces a very sharp representation of the marker element, since the latter has a good absorption for X-rays. The formed representation of the implant itself, however, is less sharp.

When said image is digitalized, the orientation of the axis of said support is determined for example by calculating the centre of gravity of the different pixels formed by the support, more particularly by said bar. The centre of the image of the marker element, or the middle point when the latter is spherical, and the centre of gravity of the support are situated on the axis of the latter. Thus, by determining the position of the centre of gravity of the bar and of the centre point of the marker element, the central axis of the implant will be known, as this axis coincides with the axis of the bar.

In a variant of the method according to the invention, it is possible, for example, to determine the centre of gravity of the image formed by the implant itself instead of that of said bar. For the centre of gravity of the image of the implant is situated on the common axis of the implant and of said bar as well. This variant is particularly interesting when the bar is highly transparent to X-rays.

The axis of the above-mentioned bar is preferably determined by drawing a fictive straight line parallel to an edge of the formed image of said bar. The latter edge extends according to the longitudinal direction of the bar. In order to obtain a precise position-finding of the implant, one has to make sure that the selected straight line goes through the centre point of the marker element. The thus determined straight line coincides with the axis of the bar and thus also with the longitudinal axis of the implant.

Consequently, in this manner is known the position and orientation of the longitudinal axis of the implant, and thus of the above-mentioned support, in relation to the jaw. Next, the exact position of the implant on this longitudinal axis is calculated on the basis of the previously determined distance between the marker element and the far end of the support which is fixed to the free end of the implant. Consequently, when the support is formed of a bar which is connected to a bearing surface of said free end of the implant, the position of this bearing surface and thus of the implant can be calculated in a simple manner.

The above-described method can also be applied to the aforesaid production model. Thus is avoided that said marker elements must be provided in the oral cavity of a patient.

FIG. 1 schematically represents the head 1 of an implant 2, together with a marker element 3 which is provided in a cylindrical support 4. Further, this figure represents a cylindrical connecting piece with a second marker element 6 which is formed of a sleeve 5 whose diameter corresponds to that of the support 4.

The top face 7 of the head 1 of the implant 2 has a triangular recess 8. The implant 2 has a cylindrical bore 9 whose axis corresponds to the longitudinal axis 10 of the implant. This bore 9 is internally threaded and opens into the bottom of said recess 8.

In order to determine the position and orientation of the implant 2 in a jaw, said marker element 3 is fixed to the implant 2 according to the invention. To this end, this marker element 3 is embedded in a cylindrical support 4. The marker element 3 consists for example of a little ball of tantalum with a diameter of 1 to 3 mm, and it is provided on the longitudinal axis 10' of the support 4 on the free end of this support 4. This free end is situated opposite to the far end of the support 4 with which the latter has to be fixed to the implant 2.

The far end of the support 4, opposite to the free end where the marker element 3 is embedded, is connected to a cylindrical securing pin 11 which is coaxial to the support 4. This securing pin 11 is externally threaded, such that it can be mounted in said bore 9 of the implant 2.

When the support 4 is thus screwed in the implant 2 via said securing pin 11, the longitudinal axis 10' of the support coincides with that of the implant 2, such that the middle point or the centre point of said marker element 3 is situated on the longitudinal axis 10 of the latter as well.

When the position and orientation of the implant 2 in relation to the jaw in which it is fixed must be determined, a three-dimensional X ray will for example be made of the jaw with the implant 2 and said support 4 which is mounted on the latter. Hereby is made sure that the support 4 with its far end 12 which is provided with the above-mentioned securing pin 11, rests on the top face 7 of the head 1 of the implant 2.

For clarity's sake, FIG. 2 represents a two-dimensional image of an X ray of the implant 2 and the support 4. In this image, the support 4 and the marker element 3 are clearly discernable. The implant 2, which is fixed in the bone of a jaw 13, does not produce a sharp image, however. Thus, in order to determine the position and orientation of the implant, an imaginary straight line is drawn through the middle point of the marker element 3 and parallel to the edge 14 of the image of the cylindrical support 4. Consequently, this imaginary straight line coincides with the longitudinal axis 10 of the implant 2, such that the orientation of the implant 2 in relation to the jaw 13 is known.

On the basis of the previously determined distance (d) between the marker element 3 and the far end of the support 4, which rests on the head 1 of the implant 2, the position of the implant 2 is then calculated in relation to the jaw 13.

When one wishes to determine the angular position of the implant 2 in relation to its longitudinal axis 10 as well, the above-mentioned sleeve 5 is provided between the implant 2 and the support 4.

The sleeve 5 is provided with a protrusion 15 whose shape and dimensions practically correspond to those of the above-mentioned recess 8, such that this protrusion 15 can be placed in the recess 8 in a practically fitting manner.

Further, the sleeve 5 has a preferably cylindrical recess 16 which extends through the entire thickness thereof and through said protrusion 15, such that the securing pin 11 can be put through said recess 16 and can be fixed in said bore 9. The length of the securing pin 11 is thus larger than the thickness of the sleeve 5 with the protrusion 15 in the direction of the axis of said recess 16. The sleeve 5 is hereby clamped between the head 1 of the implant 2 and said far end 12 of the support 4. Consequently, the support 4 is coaxial to the implant 2.

The sleeve 5 itself rests, as already mentioned above, on the top face 7 of the head 1 of the implant 2. The distance between the side 12' of the sleeve 5, designed to be connected to the head 1 of the implant 2, and said marker element 3, which is embedded in the support 4, is hereby determined beforehand in order to calculate, as has already been described above, the three-dimensional position of the implant 2 on the basis of said distance.

Said second marker element 6 is embedded in the sleeve 5 at a certain distance from the longitudinal axis 10 of the implant 2. The position of the second marker element 6 in relation to said recess 8 in the head of the implant 2 is hereby determined, and preferably also in relation to the longitudinal axis 10 thereof.

When an image is thus formed, for example by means of X-rays, of the jaw with the implant 2, the sleeve 5 with the second marker element 6 and the support 4, the angular position of said recess 8, or of the protrusion 15 in relation to the longitudinal axis 10, is determined on the basis of the observed position of the image of the second marker element 6. Consequently, the angular position of the implant 2 in relation to the axis 10 thereof can be determined in this manner, such that its entire position is known.

Although said recess 8 in this embodiment of the implant 2 has a triangular section according to a cross direction in relation to the longitudinal axis 10, this recess 8 may assume very different shapes. Thus, said section may also be elliptic, square or polygonal.

Further, said support 4 must not necessarily have a circular cross section, but this section may be elliptic or polygonal as well.

The invention is not restricted to the above-described embodiments of the method and the marker element according to the invention.

Of course, it is possible to provide two or several marker elements in one and the same support which are placed at a certain distance from each other or from the side thereof which is designed to be connected to the implant. These marker elements cannot be spherical. Further, when two spherical marker elements are used, situated on the axis of one and the same cylindrical support, they may have different diameters. Thus, the position of the implant is determined univocally by the distance in relation to these marker elements and by the orientation and position of the connecting line connecting the middle points of the marker elements.

The invention claimed is:

1. A method to determine a position of a dental implant (2) having a central axis (10), said dental implant being fixed in the bone of the jaw (13) of a person, comprising the steps of:
   after having fixed the implant into the bone of the jaw, fixing at least one marker element (3) which produces a strong contrast in imaging techniques to a free end (1) of said implant (2) in a detachable manner to situate the marker element (3) at a distance (d) from the free end (1),
   generating an image of the jaw or of a reproduction model of the jaw by means of X-rays or magnetic resonance, wherein the jaw contains the implant (2) with said marker element,
   determining the position of the marker element (3) in relation to the jaw on the basis of said image which is formed by said X-rays or by said magnetic resonance, and
   identifying the position of said implant (2) from an observed position of the marker element (3); and
   determining the position of the dental implant in relation to the jaw comprising calculating an exact position of the implant on a longitudinal axis of the implant on the basis of a previously determined distance between the marker element and the free end of the implant.

2. The method according to claim 1, the step of fixing the at least one marker element to the implant further comprises fixing a support (4) containing said marker element (3) to said implant (2) in a detachable manner.

3. The method according to claim 2, the step of fixing the support to the dental implant further comprises fixing said support (4) containing the marker element (3) to the free end (1) of said implant (2), such that said support (4) extends in a prolongation of the implant (2) and the marker element (3) is situated at a distance (d) from the free end (1).

4. The method according to claim 2, wherein said support is made of a material which is transparent to X-rays.

5. The method according to claim 3, wherein the orientation and position of said central axis (10) of the implant (2) is determined by defining a straight line through a centre point of said marker element (3) which is parallel to a longitudinal side (14) of a representation of said support (4) in said image.

6. The method according to claim 3, further comprising the step of:
   determining the orientation and position of said central axis (10) of the implant (2) by defining a centre of gravity of pixels representing the implant (2) or said support (4) in said image and by defining a centre of gravity of a representation of said marker element (3) in said image, whereby these centres of gravity are then mutually connected by means of a straight line.

7. The method according to claim 6, wherein the step of determining the position of the dental implant in relation to the jaw is based on the orientation and the position of said central axis (10) of the implant (2) and the distance (d) between said marker element (3) and said free end (1) of the implant (2).

8. The method according to claim 1, wherein a second marker element (6) is fixed in relation to the implant (2), with a centre point which is not situated on said central axis (10) of said implant (2), wherein, on a basis of the observed position of the second marker element (6), an angular position of the implant (2) in relation to said central axis (10) is determined.

9. The method according to claim 1, wherein said marker element (3, 6) is spherical.

10. The method according to claim 1, wherein said marker element (3,6) contains at least tantalum, platinum or tungsten.

11. The method according to claim 1, wherein said image is formed by means of X-ray computed tomography.

12. The method according to claim 1, wherein the dental implant (2) is made of titanium.

13. A support with a marker element (3,6) for determining the position of a dental implant (2) which is fixed to a jaw (13) of a person, in relation to said jaw (13), wherein the marker element (3,6) produces a strong contrast in an image generated by X-rays or magnetic resonance compared to said implant (2) itself,
  wherein said support is mainly formed of a material which is transparent to X-rays,
  wherein the support (4) has means at one far end to be fixed to said implant (2) in a detachable manner, whereas the other far end of the support (4) comprises said marker element (3,6),
  wherein said means for fixing the support to the implant (2) comprise a securing pin (11), and
  wherein the support comprises a sleeve (5) with a protrusion (15) whose dimensions correspond practically to those of a recess (8) provided in a head (1) of the implant (2) on which this support must be fixed, such that said protrusion (15) can be placed in a practically fitting manner in said recess (8),
  wherein said sleeve (5) presents a second marker element (6) having a centre point which is not situated on the central axis of the sleeve.

14. The support according to claim 13, wherein said securing pin (11) is coaxial to the support.

15. The support according to claim 13, wherein said securing pin (11) is externally threaded.

16. The support according to claim 13, wherein said marker element (3,6) contains at least one of the metals from the group formed of tantalum, platinum and tungsten.

* * * * *